United States Patent [19]

Clouse

[11] Patent Number: 5,211,658
[45] Date of Patent: May 18, 1993

[54] METHOD AND DEVICE FOR PERFORMING ENDOVASCULAR REPAIR OF ANEURYSMS

[75] Inventor: Melvin E. Clouse, Brookline, Mass.

[73] Assignee: New England Deaconess Hospital Corporation, Boston, Mass.

[21] Appl. No.: 788,799

[22] Filed: Nov. 5, 1991

[51] Int. Cl.[5] ............................................. A61F 2/06
[52] U.S. Cl. ........................................ 623/1; 623/12; 606/191; 606/198
[58] Field of Search ............... 606/198, 191, 108, 153, 606/155, 156; 623/1, 12

[56] References Cited

U.S. PATENT DOCUMENTS

| | | | |
|---|---|---|---|
| 3,657,744 | 4/1972 | Ersek | 3/1.3 |
| 3,868,956 | 3/1975 | Alfidi . | |
| 4,130,904 | 12/1978 | Whalen | 3/1.4 |
| 4,140,126 | 2/1979 | Choudhury | 125/325 |
| 4,306,318 | 12/1981 | Mano et al. | 3/1.4 |
| 4,416,028 | 11/1983 | Eriksson et al. | 3/1.4 |
| 4,441,215 | 4/1984 | Kaster | 3/1.4 |
| 4,503,569 | 3/1985 | Dotter . | |
| 4,512,338 | 4/1985 | Balko et al. | 128/1 |
| 4,550,447 | 11/1985 | Seiler, Jr. et al. | 623/1 |
| 4,562,596 | 1/1986 | Kornberg | 623/1 |
| 4,577,631 | 3/1986 | Kreamer | 128/334 |
| 4,601,718 | 7/1986 | Possis et al. | 623/1 |
| 4,619,641 | 10/1986 | Schanzer | 604/8 |
| 4,629,458 | 12/1986 | Pinchuk | 623/1 |
| 4,655,771 | 4/1987 | Wallsten | 623/1 |
| 4,665,906 | 5/1987 | Jervis | 128/92 |
| 4,733,665 | 3/1988 | Palmaz | 128/343 |
| 4,739,762 | 4/1988 | Palmaz | 128/343 |
| 4,776,337 | 10/1988 | Palmaz | 128/343 |
| 4,798,606 | 1/1989 | Pinchuk | 623/1 |
| 4,820,298 | 4/1989 | Leveen et al. | 623/1 |
| 4,830,003 | 5/1989 | Wolff et al. | 128/343 |
| 4,856,516 | 8/1989 | Hillstead | 128/343 |
| 4,878,906 | 11/1989 | Lindemann et al. | 623/1 |
| 4,886,062 | 12/1989 | Wiktor | 128/343 |
| 4,954,126 | 9/1990 | Wallsten . | |
| 4,969,896 | 11/1990 | Shors | 623/1 |
| 4,992,905 | 5/1990 | Strecker | 606/195 |
| 4,994,071 | 2/1991 | MacGregor | 606/194 |
| 4,998,539 | 3/1991 | Delsanti . | |
| 5,015,253 | 5/1991 | MacGregor | 623/1 |
| 5,019,085 | 5/1991 | Hillstead | 606/108 |
| 5,019,090 | 5/1991 | Pinchuk | 606/194 |
| 5,035,706 | 7/1991 | Gianturco . | |
| 5,123,917 | 6/1992 | Lee | 623/1 |

FOREIGN PATENT DOCUMENTS 0183372 10/1985 European Pat. Off. .

OTHER PUBLICATIONS

Barth, et al., "Flexible Tantalum Stents Implanted in Aortas and Iliac Arteries: Effects in Normal Canines"; *Radiology* 1990, 175:91–96.

Strecker et al., "Expandable Tubular Stents for Treatment of Arterial Occlusive Diseases: Experimental and Clinical Results"; *Radiology* 1990, 175:97–102.

Mirich, et al., "Percutaneously Placed Endovascular Grafts for Aortic Aneurysms: Feasibility Study", *Radiology* 1989, 170:1033–1037.

Lawrence, et al. Percutaneous Endovascular Grat: Experimental Evaluation.

Palmaz, et al., "Expandable untraluminal vascular graft: A feasibility study" *Surgery* 1986, 99:199-2-5.

Palmaz, et al., "Atherosclerotic Rabbit Aortas: Expandable Intraluminal Grafting", *Radiology* 1986, 160:723–726.

Palmaz, et al., "Expandable Intraluminal Graft: A Preliminary Study", *Radiology* 1985, 156:73–77.

Wright, et al., "Percutaneous Endovascular Stents: An Experimental Evaluation", *Radiology* 1985, 156:69–72.

Cragg, et al., "Percutaneous Arterial Grafting", *Radiology* 1984, 150:45–49.

Cragg, et al., "Nonsurgical placement of Arterial Endoprosteses: A New Technique Using Nitinol Wire"; *Radiology*, 1983, 147:261–263.

Dotter et al, "Transluminal Expandable Nitinol Coil Stent Grafting: Preliminary Report", *Radiology* 1983, 147:259–260.

Mills, et al., "Aortic Dissection: Surgical and Nonsurgical Treatments compared", *The American Journal of Surgery* 1979; 137:240–243.

Blakemore, et al., "Recent Advances in Surgery", *Surgery*.

Voorhees, et al., "The Use of Tubes Constructed From Vinyon N Cloth in Bridging Arterial Defects", *Ann. of Surgery* 1952; 135:332–336.

Edwards, et al., "A Safer Technique For Replacement Of The Entire Ascending Aorta and Aortic Value" *The Journal of Thoratic And Cardiovascular Surgery*, 1970; 59:837.

Liotta et al., "Surgical Treatment of Acute Dissecting Aneurysm of the Ascending Aorta": *Animals Thoracic Surgery* 1971; 12:582–592.

Parker Jr. et al., "Management of the Acute Aortic Dissection", *Annals Thoracic Surgery*; 19:436.

Ablaza, et al, "Use of a ringed intraluminal graft in the surgical treatment of dissecting aneurysms of the Thoracic Aorta", *J. Thor. and Cardiovascular Surgery*; 76:390–396.

Dureau, et al. "New Surgical Technique For the Operative Management of Acute Dissections of the Ascending Aorta"; *J. Thoracic and Cardiovascular Surgery* 1978; 25:250–253.

Koster et al, "Late Results of operation for Acute Aortic Dissection Production Aortic Insufficiency" *Annals of Thoracic Surgery* 1978; 26:461–467.

Berger, Robert L., "A Simplified Plastic Repair for Aortic Dissections", *Annals of Thoracic Surgery* 1978; 25:250–253.

Product literature by Bard Implants Division and Meadox Medical Inc.

*Primary Examiner*—Michael H. Thaler
*Attorney, Agent, or Firm*—Fish & Richardson

[57] ABSTRACT

A blood vessel wall-defining device and method for using the device for repairing an aneurysm. The device comprises in combination, a percutaneously-insertable structural frame extending between first and second ends having an unexpanded diameter which is smaller than the diameter of the blood vessel to allow the structural frame to be percutaneously placed into the blood vessel, the structural frame being expansible to form a generally cylindrical structural skeleton having a slightly larger diameter than the blood vessel to facilitate the securing of the structural skeleton in position in the blood vessel, and an independently, percutaneously-insertable, expansible tubular member extending between first and second ends constructed to be percutaneously placed subsequent to the placement of the structural frame, the tubular member comprising a thin-walled flexible tubular membrane extending between the first and second ends of the tubular member, the thin-walled flexible tubular membrane being essentially impermeable to blood and blood products, and means for expanding and holding the thin-walled flexible tubular membrane adjacent the inside of the structural skeleton, in a cooperative relationship therewith, in a manner that the outer surface of the thin-walled flexible tubular membrane is held in secure contact with the inside of the previously-placed structural skeleton.

22 Claims, 3 Drawing Sheets

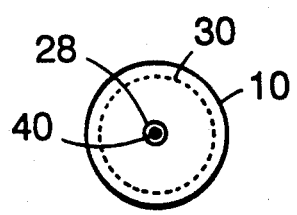
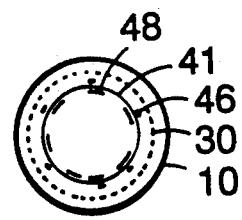
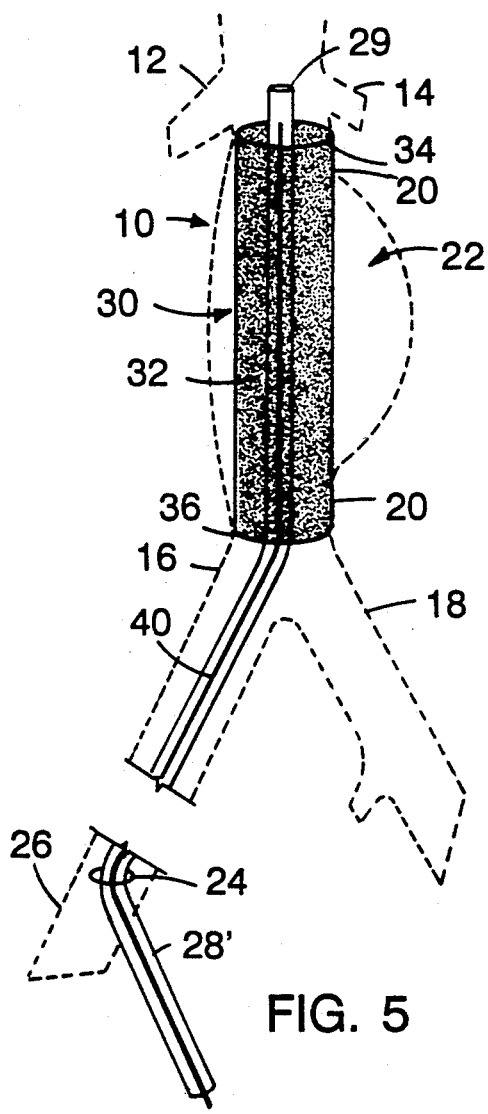
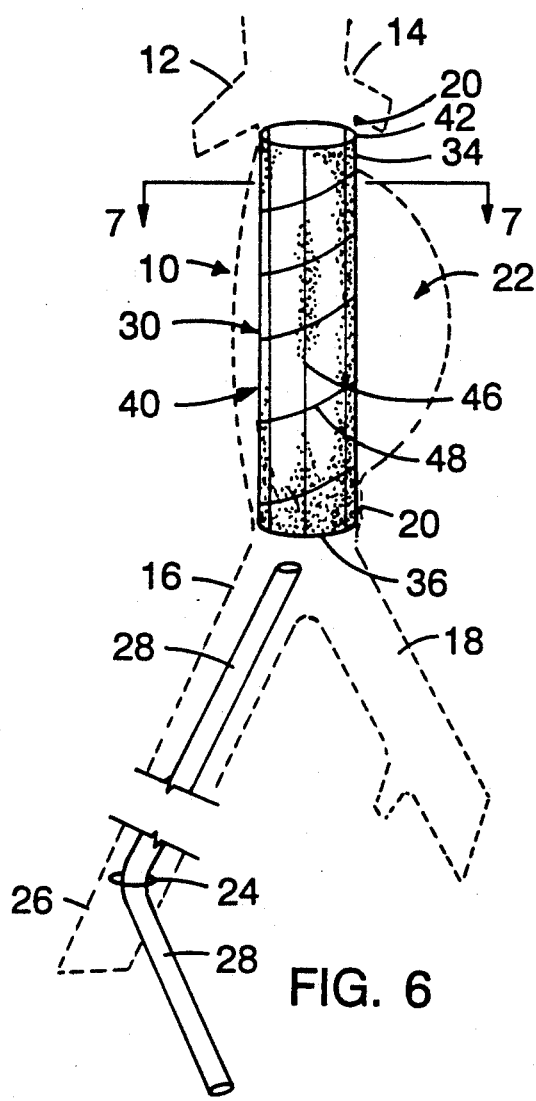

METHOD AND DEVICE FOR PERFORMING ENDOVASCULAR REPAIR OF ANEURYSMS

BACKGROUND OF THE INVENTION

This invention relates generally to blood vessel wall-defining techniques and more specifically to a device and method capable of repairing aneurysms in large vessels employing percutaneous insertion.

Approximately 70% of the aneurysms reported in the United States each year are repaired by the conventional open surgical technique known as aneurysmectomy. However, the mortality rate associated with aneurysmectomy remains relatively high, 12.9% for elective surgery, 30–50% for emergency surgery after vascular rupture, and as high as 71% for patients over 70 years of age (Ruckley, In: The Cause and Management of Aneurysms, Greenhalgh R. M. et al. eds, W. B. Saunders, Philadelphia, p. 327–337, 1990; Lawrie et al., Surgery 85:483, 1979). Some of the factors involved in the high operative mortality rate are underlying coronary or cerebral atherosclerosis, severe obstructive pulmonary disease, and renal disease.

Another major disadvantage of aneurysmectomy is that, because of the nature of the operation, it can only be performed in medical facilities which have the sophisticated equipment necessary to perform major cardiovascular surgery. In cases where the prognosis for rupture is imminent, fatalities may occur because of insufficient time to perform diagnostic studies and/or transfer the patient to a major medical center where surgery can be performed. Therefore, there has been a long felt need for simpler, quicker and less traumatic techniques for repairing aneurysms.

Percutaneous techniques of blood vessel repair such as introducing vascular stents into arteries or veins have been suggested, and have had some significant application, but known approaches have certain drawbacks and/or limitations and thus, have not found wide use with respect to large vessels, especially the abdominal aorta where a significant number of aneurysms occur.

SUMMARY OF THE INVENTION

The present invention provides a blood vessel wall-defining device, and a method for insertion of the wall-defining device within a blood vessel of an animal, preferably a human patient, which has an abnormal widening, or aneurysm, along a section of the vessel wall. The invention is particularly applicable to aneurysms in an aorta, especially in the abdominal aorta below the conjunction of the renal arteries and above the bifurcation of the aorta into the common iliac arteries.

According to a first aspect of the invention a blood vessel wall-defining device for repairing an aneurysm comprises in combination, a percutaneously-insertable structural frame extending between first and second ends having an unexpanded diameter which is smaller than the diameter of the blood vessel to allow the structural frame to be percutaneously placed into the blood vessel, the structural frame being expansible to form a generally cylindrical structural skeleton having a slightly larger diameter than the blood vessel to facilitate the securing of the structural skeleton in position in the blood vessel, and an independently insertable, expansible tubular membrane extending between first and second ends, which is constructed to be inserted subsequent to the structural frame. The tubular member comprises a thin-walled flexible tubular membrane extending between the first and second ends which is essentially impermeable to blood and blood products, and means for expanding and holding the thin-walled flexible tubular membrane adjacent to the inside of the structural skeleton, in a cooperative relationship therewith, in a manner that the outer surface of the thin-walled flexible tubular membrane is held in secure contact with the inside of the previously placed structural skeleton.

In an extremely important aspect of the invention, the blood vessel wall-defining device is used for repairing an aneurysm in the aorta. In this aspect, the structural skeleton has an expanded diameter of the order of 2 centimeters or more, the expanded diameter being slightly larger than the diameter of the aorta, the first and second ends of the structural skeleton are spaced about 10 centimeters or more apart and the distance between the first and second ends of the tubular member substantially correspond to the distance between the first and second ends of the structural skeleton.

In preferred embodiments, the structural frame has one or more of the following features.

The structural frame comprises first and second axially spaced end rings, each of the rings being expansible to form a relatively stable retaining formation.

The axially spaced end rings additionally comprise hooks constructed to engage the tissue of the vessel wall to aid in the securing of the rings to the inner wall of the blood vessel.

The structural frame additionally comprises a plurality of strands arranged in a skeleton-defining pattern, the pattern extending between the first and second ends and joined to the axially spaced end rings. Preferably, the pattern of strands is of mesh form.

Most preferably, the strands and the rings of the structural frame are comprised of shape memory metal having a pliable low temperature state in which the structural frame is in unexpanded condition, and an expanded resiliently deformable relatively high temperature state, the high temperature corresponding to the body temperature of a mammal.

According to another aspect of the invention, an expansible tubular member is provided for independent insertion within an expanded structural skeleton previously placed within a blood vessel. In this aspect of the invention, the tubular member comprises an expansible thin-walled flexible tubular membrane extending between first and second ends which is essentially impermeable to blood and blood products, and includes means for expanding and holding the thin-walled flexible tubular membrane adjacent to the inside of the structural skeleton, in a cooperative relationship therewith, in a manner that the outer surface of the thin-walled flexible tubular membrane is held in secure contact with the inside of the structural skeleton.

In preferred embodiments of the first and second aspects of the invention, the expansible tubular member has one or more of the following features.

The means for expanding and holding the thin-walled flexible tubular membrane of the tubular member comprises first and second axially spaced rings joined to the first and second ends of the thin-walled flexible tubular membrane, each of the rings being expansible to form a relatively stable retaining formation.

In certain instances, the means for expanding and holding the thin-walled flexible tubular membrane also comprises struts axially disposed on the exterior of the thin-walled flexible tubular membrane, the ends of the struts being joined to the axially spaced first and second rings.

In other instances, the means for expanding and holding the thin-walled flexible tubular membrane further comprises an expansible, open structural means disposed within the interior of the thin-walled flexible tubular membrane and constructed to prevent the inward collapse of the thin-walled flexible tubular membrane from its expanded form. Preferably, open structural means is an outwardly expansible spring coil, and preferably the coil extends between the first and second axially spaced rings, respective ends of the coil being joined to the axially spaced rings.

In certain preferred embodiments, the means for expanding and holding the thin-walled flexible tubular membrane of the tubular member comprises the combination of first and second axially spaced rings joined to the first and second ends of the thin-walled membrane, each of the rings being expansible to form a relatively stable combination, struts axially disposed on the exterior of the thin-walled membrane, the ends of the struts being joined to the axially spaced rings, and an expansible, open structural means disposed within the interior of the thin-walled membrane constructed to prevent the inward collapse of the thin-walled membrane from its expanded form.

In the preferred embodiments of the invention, the rings, the struts, and the open structural means of the tubular member are comprised of shape memory metal having pliable low temperature state in which the tubular member is in unexpanded condition, and an expanded resiliently deformable and relatively high temperature state, the high temperature corresponding to the body temperature of a mammal.

In preferred embodiments, the thin-walled flexible tubular membrane comprises nylon mesh.

Additionally, the device may include insertion means for independently inserting the tubular member into the previously placed structural skeleton, and preferably the insertion means comprises an insertion catheter in which the tubular member is confined in reduced size for percutaneous insertion into the body.

The invention also features a two-step placement method for repairing an aneurysm in a blood vessel via interventional radiological techniques.

The first-step of the method of the invention comprises determining the length of the aneurysm and the diameter of the blood vessel, providing a structural frame extending between first and second ends having a diameter which is smaller than the diameter of the blood vessel, the structural frame being expansible to form a generally cylindrical structural skeleton having a slightly larger diameter than the blood vessel, inserting the structural frame percutaneously in unexpanded form into the blood vessel at a site proximal or distal to the aneurysm and moving the structural frame to the site of the aneurysm, causing the expansion of the frame to form the structural skeleton, and anchoring at least the first and second ends to the walls of the blood vessel above and below the aneurysm.

The second-step of the method of the invention comprises providing an expansible tubular member extending between first and second ends, the tubular member comprising a thin-walled flexible tubular membrane extending between the first and second ends, the thin-walled flexible tubular membrane being essentially impermeable to blood and blood products, and means for expanding and holding said thin-walled flexible tubular membrane adjacent to the inside of said structural skeleton, independently inserting the tubular member percutaneously in unexpanded form into the blood vessel at a site distal to the aneurysm and moving the tubular member into the structural skeleton previously disposed within the blood vessel, and causing the expansion and anchoring of the tubular member adjacent the inside of the structural skeleton, the outer surface of the tubular member engaging the structural skeleton, whereby the combination of the structural skeleton and the tubular member cooperate to define a graft-form section of the blood vessel that isolates the aneurysm from hemodynamic pressure.

In an extremely important embodiment, the method of the invention is used to repair an aortic aneurysm. The structural frame is expansible to form a generally cylindrical structural skeleton having an expanded diameter of the order of 2 centimeters or more, the expanded diameter being slightly larger than the diameter of the aorta, the distance between the first and second ends of the structural skeleton of about 10 centimeters or more, and the distance between the first and second ends of the tubular member substantially correspond to the distance between the first and second ends of the structural skeleton. When the method of the invention is used to repair an aneurysm in the abdominal aorta the distance between the first and second ends corresponds approximately to the distance between the conjunction of the renal arteries and the bifurcation of the aorta into the common iliac arteries.

The objective of the present invention is to provide a blood vessel wall-defining device for placement at the site of an aneurysm using percutaneous techniques, thus obviating the need for surgically removing and replacing the defective blood vessel.

Another objective of the present invention is to provide a method for performing aneurysmal repair which has a lower mortality rate than conventional surgery. This method does not require general anesthesia or major surgery and therefore may be performed even on patients which are at high risk due to other complicating factors. Due to the relative non-invasiveness of the method of the invention, aneurysm repair can be accomplished in a short period of time with less patient trauma, thus reducing the cost of prolonged hospitalization and intensive care treatment.

Other features and advantages of the invention will be apparent from the following description of the preferred embodiments, and from the claims.

DETAILED DESCRIPTION

The drawings will first be briefly described.

FIG. 5 is a diagrammatic sectional view of an abdominal aorta showing the method of insertion of the flexible thin-walled tubular membrane within the outer structural skeleton while FIG. 5a is a diagrammatic end view of the member.

FIG. 6 is a diagrammatic sectional view of an abdominal aorta showing both the structural skeleton and thin-walled flexible tubular membrane of the blood vessel wall-defining device of the invention in fully expanded form while FIG. 6a is a diagrammatic end view of the member.

Figure 1:
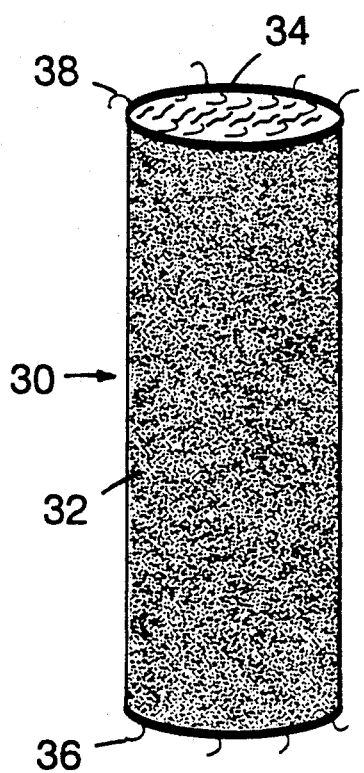
FIG. 1 is a perspective view of a preferred embodiment of the structural frame of the invention expanded to form the outer structural skeleton of the blood vessel wall-defining device of the invention.
Figure 3:
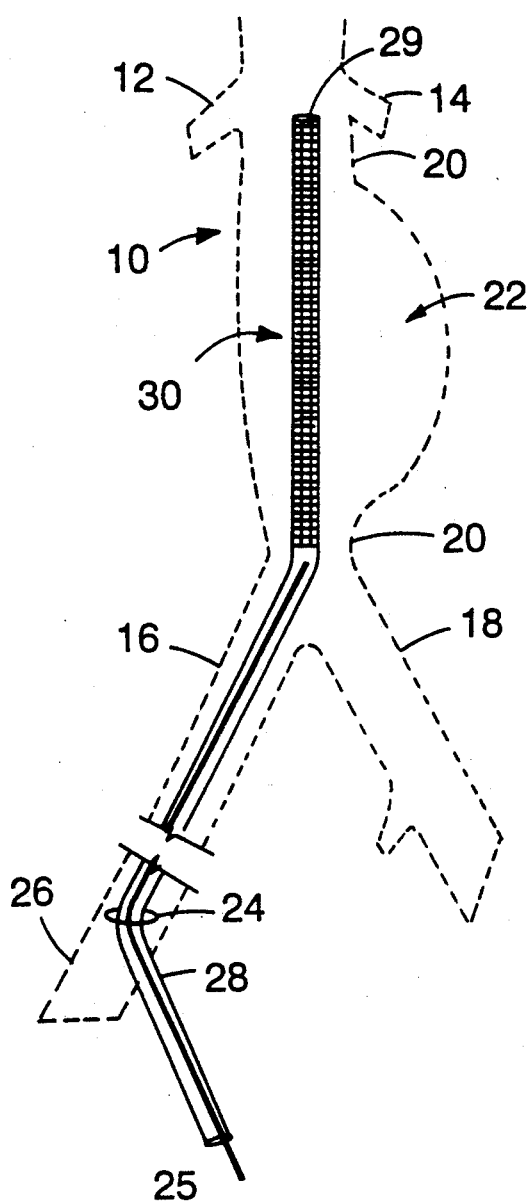
FIG. 3 is a diagrammatic sectional view of an abdominal aorta showing the method of insertion and placement of the outer structural frame of the blood vessel wall-defining device of the invention.
Figure 4:
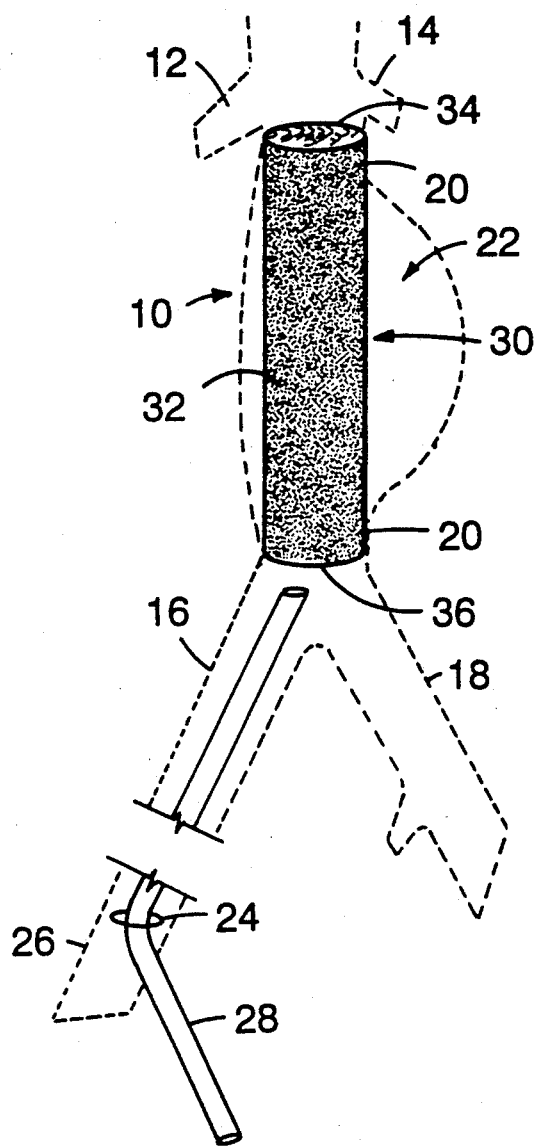
FIG. 4 is a diagrammatic sectional view of an abdominal aorta showing the outer skeleton in place in the aorta in its expanded state.

Referring to FIGS. 1, 3 and 4 the presently preferred embodiment of the present invention features, as one component of a blood vessel wall-defining device, a structural skeleton 30 of generally cylindrical form sized for placement in the abdominal aorta below the conjunction of the renal arteries and above the bifurcation of the aorta into the common iliac arteries. It is constructed of a plurality of fine metal wires 32 arranged to form a mesh which is attached to axially spaced end rings 34 and 36. Preferably, rings 34 and 36 each have a groove on their inner surface. The wires 32 are approximately 0.013 inch in diameter and the rings 34 and 36 are comprised of wire of approximately 0.026 inch diameter. Both wires 32 and rings 34 and 36 are of a shape memory alloy which is relatively soft and pliable at low temperatures (below body temperature), and that assumes and retains an expanded, resiliently deformable and relatively stable shape of diameter, e.g., of about 2 centimeters, and length, e.g., of about 10 centimeters at a high temperature, (i.e. at body temperature). A suitable material is an alloy of nickel and titanium, generally referred to as "Nitinol" (Nitinol Medical Technologies, Inc.). This material is described in Jackson et al. "55-Nitinol - The alloy with a Memory: Its Physical Metallurgy, Properties, and Applications, A Report,"NASA-SP 5110, Technology Utilization Office, National Aeronautics and space Administration (1972), and Simon, U.S. Pat. No. 4,425,908, both hereby incorporated as reference. Nitinol is very inert and is therefore unlikely to cause adverse reactions within the body. A particular alloy which has the temperature characteristics preferred for the graft of the invention is 55.1 weight percent nickel with the balance being titanium. The low-temperature phase of this particular alloy exists below 70° F. and the high-temperature phase exists above 90° F. In its low-temperature state, the structural skeleton 30 is straightened and compressed to enable confinement within a catheter positioned in the blood vessel, see FIG. 3.

A plurality of retaining hooks 38 are spaced circumferentially about and secured to each of the axially spaced end rings 34 and 36. In the preferred embodiment, the hooks 38 are constructed of Nitinol but may also be constructed of rigid plastic, stainless steel, or other biologically acceptable material. When the structural skeleton 30 is positioned in the blood vessel in expanded form, see FIGS. 1 and 4, hooks 38 become embedded in the wall tissue of the blood vessel and aid in securing the structural skeleton 30.

Figure 2:
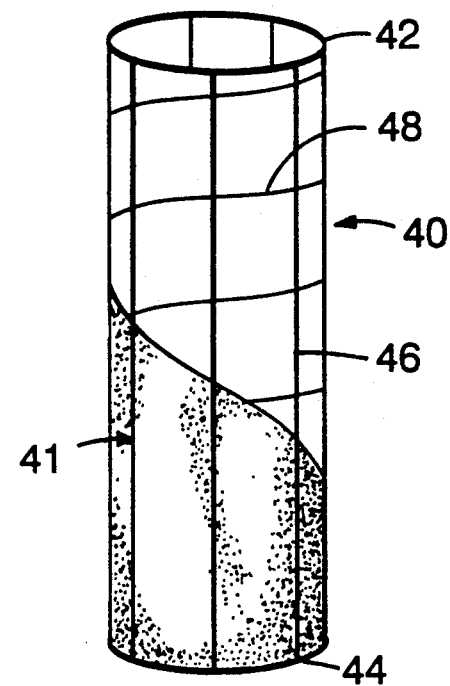
FIG. 2 is a perspective view of a preferred embodiment of the flexible thin-walled tubular membrane of the blood vessel wall-defining device of the invention in expanded form
Figure 7:
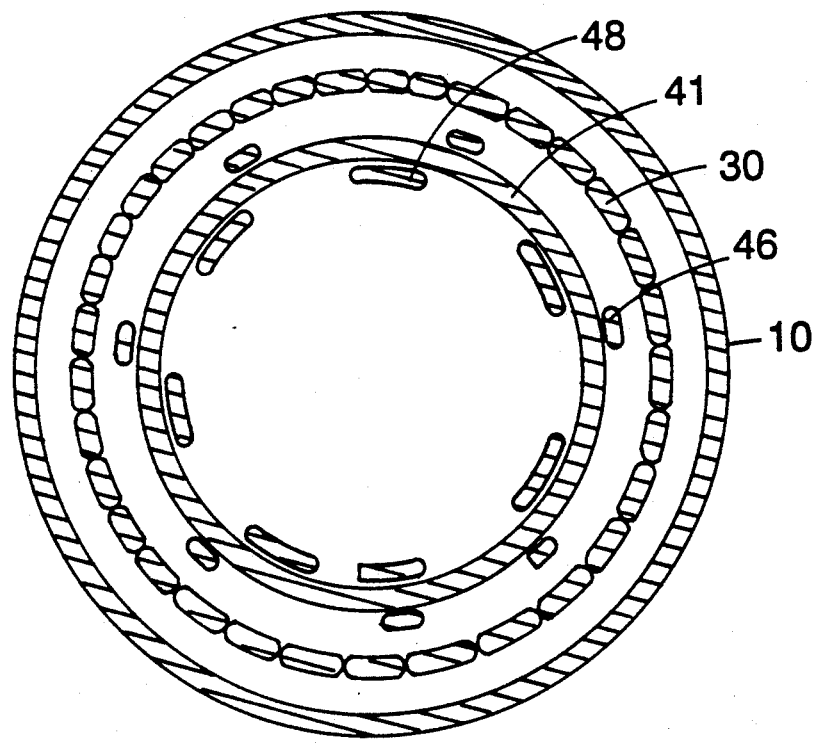
FIG. 7 is a view similar to FIG. 6a of expanded scale.

Referring to FIG. 2, the blood vessel wall-defining device also comprises, as a second component, an expansible tubular member 40 which is constructed for placement inside of the previously-placed structural skeleton 30 shown in FIGS. 1 and 4. The tubular member 40 is constructed of a membrane 41 which is composed of a material which is collapsible, such as nylon having a mesh size sufficiently fine to provide patency during use, similar to that provided in known vascular grafts. The material should be essentially impermeable to blood and blood products or capable of becoming essentially impermeable shortly after placement in the body, e.g., by deposition of fibrin into the material. The material of this tubular member 40, and all other components entering the body must be sufficiently inert to permit safe insertion. At each end of the tubular membrane 40 are axially spaced rings 42 and 44. The rings 42 and 44 are of slightly smaller diameter than rings 34 and 36 of the structural skeleton and in the presently preferred embodiment are joined to membrane 41 and designed to fit within and lock into the grooves in rings 34 and 36. Alternatively, the tubular member may be secured by small hooks on protruberances on the inner surface of the structural skeleton. Disposed on the exterior of the thin-walled flexible tubular membrane 41 are struts 46 (four to eight depending e.g. upon size of the device as well as upon the thickness and material of the individual struts) attached to rings 42 and 44. Disposed on the interior of thin-walled tubular membrane 41 is an outwardly expansible spring coil 48, attached to rings 42 and 44. The spring 48 has between 4 and 6 turns over the length of the coil and is constructed to prevent the inward collapse of the thin-walled flexible tubular membrane 41 once it is in expanded form within the structural skeleton. The rings 42 and 44, the struts 46, and the coil 48 are preferably constructed of Nitinol.

In utilizing the device of the present invention to repair an aneurysm, appropriate diagnosis is first made to determine the location and size of the aneurysm. Diagnostic procedures include physical examination, x-ray, and ultrasound. Once the diameter of the blood vessel and the length of the aneurysm has been determined, a device of the appropriate diameter and length is chosen to repair the aneurysm.

The example described below refers to an aneurysm in the abdominal aorta for the purpose of illustration of an extremely important and demanding application while it is not intended to limit the scope of the broadest aspects of the invention.

Referring to FIG. 3, the abdominal aorta 10 is indicated generally although it will be appreciated that the drawing is intended to be illustrative and is not a scale drawing. Renal arteries 12 and 14 extend from aorta 10 and the latter divides into the common iliac arteries 16 and 18 at its lowermost end. Aorta 10 is a major blood-carrying vessel of the body and is characterized throughout most of its length by healthy tissue 20 which presents the artery wall. A damaged segment of aorta 10 is indicated at 22 where a large aneurysm has formed.

To initiate insertion of the blood vessel wall-defining device according to the method of the invention, a perforation 24 is formed using a needle and appropriate dilators (not shown) at a location distal from the aneurysm, preferably in the femoral artery 26 below the groin. If the femoral artery 26 is closed or if the location dictates, the carotid or axillary arteries (not shown) may instead be used.

To determine the exact diameter and length of the aorta, an initial x-ray contrast aortogram is performed using standard catheter techniques and cut film. A pigtail catheter (not shown) is generally used with filming at the rate of 2/Sec×3 and 1/Sec×6. A calibrated guide wire (not shown) is then passed through the lumen of the pigtail catheter and a second standard plain film is taken to correct for magnification and to obtain essentially an exact measurement of the diameter and length of the aorta.

The calibrated guide wire is withdrawn and an exchange guide wire 25 is placed in the pigtail catheter. The pigtail catheter is then removed and a catheter 28 of 8 to 10 French diameter is passed over the guide wire 25 into the lumen of the femoral artery 26.

Under fluoroscopic guidance, the end 29 of catheter 28 is guided into the abdominal aorta 10 and positioned below the renal arteries 12 and 14 to a site judged to be optimal for the delivery of the device of the invention and the guide wire is removed leaving the catheter 28 in the artery.

A plastic infusion bag of normal saline solution (not shown) is kept at a temperature between 40° and 50° F. The bag is connected to the catheter 28 through standard tubing (not shown) to the delivery port (not shown) of the catheter 28. The cooled liquid is allowed to infuse through the catheter 28 at a steady rate controlled by an adjustable drip control device (not shown) on the tubing.

With the cold infusion drip maintaining the temperature of the catheter 28, structural skeleton 30 in its pliable, straightened low-temperature form is inserted into the catheter 28 and pushed by an appropriate pushing wire along the length of the catheter 28 into the abdominal aorta 10. Once the structural skeleton 30 reaches the proximal end 29 of the catheter 28, the catheter 28 is slowly withdrawn while the pushing wire is held fixed from a proximal position, to cause progressive extrusion of the skeleton withdrawing from the catheter 22.

As the skeleton 30 is extruded into the abdominal aorta the skeleton 30 is exposed to body temperature and progressively expands into its high-temperature cylindrical shape as it reaches body temperature (FIG. 4). As the structural skeleton 30 expands, the rings 34 and 36, which have a diameter that is slightly larger than the diameter of aorta 10, will contact the vessel wall and hooks 38 will project into the healthy artery wall 20 above and below the aneurysm 22 to retain the skeleton 30 in position.

Referring to FIGS. 5 and 6, under fluoroscopic guidance, the end 29 of catheter 28' is guided into the abdominal aorta 10 and positioned within the structural skeleton 30 at a site judged to be optimal for the delivery of the tubular member 40. The tubular member 40 is then inserted into catheter 28' and pushed forward by an appropriate pushing wire. During this action, the catheter 28' is infused with normal saline solution (not shown) kept at a temperature between 40° and 50° F., thus maintaining the structural components of the tubular member 40 in pliable low-temperature state. When the tubular membrane 40 is judged to be correctly placed within the structural skeleton 30, catheter 28 is slowly withdrawn while holding the pushing wire in place. As the tubular member 40 is extruded from catheter 28, the axial ring 42 reaches body temperature, expands and becomes interlocked with ring 34 of structural skeleton 30. Then struts 46 and coil 48 upon reaching their high-temperature state facilitate the expansion of tubular member 40 to contact the inner walls of structural skeleton 30 and prevent any subsequent collapse of tubular member 40. Finally, ring 44 expands and becomes interlocked with ring 36 of structural skeleton 30.

Once in position, the structural skeleton 30 and tubular member 40 cooperate to provide a stable, patent device which acts to isolate the aneurysm from hemodynamic pressure. Use The device of the invention serves as a permanent, effective graft to prevent further damage to the arterial wall in the area of the aneurysm. It provides a faster, less invasive method of treatment than conventional surgery, thus decreasing patient trauma and recovery time. The delivery and placement of the blood vessel wall-defining device into the aorta should take only a small fraction of time required for a conventional surgical approach. This, in turn, should decrease the mortality rate as well as the length of hospitalization and the expense of treatment.

The two-step construction of the graft of the invention provides an important advantage over one-step approaches by enabling the introduction of a device of sufficient size and stability to enable use in large vessels such as the abdominal aorta while ensuring a stable, patent graft for aneurysm repair.

OTHER EMBODIMENTS

One may construct standardized sizes of the structural skeleton and thin-walled flexible tubular membrane for packaging into kits for use in the method of the invention.

The skeleton and the thin walled member may be preinstalled in the distal ends of respective catheters and may be injected by pusher devices similar to those employed to eject vena cave filters.

The two components may be disposed in succession within the same catheter for successive extrusion-placement. Guidance features respectively on the ends of the skeleton or the thin walled member can be provided to ensure appropriate registry and retention of the respective ends of those inter-fitting components. The ends of the thin-walled flexible tubular membrane may be positioned beyond the respective ends of the skeleton.

The two components may also be introduced on the exterior of respective balloon catheter and may be expanded to final form by controlled inflation of the respective balloon, in which case the structural elements of the components may be constructed of yieldable metal that takes a permanent set deformation, in which case shape memory metal need not be employed.

Various other modifications of the invention, within the spirit thereof and the scope of the claims, will occur to those skilled in the art.

I claim:

1. A blood vessel wall-defining device for repairing an aneurysm comprising in combination,
a percutaneously-insertable structural frame extending between first and second ends having an unexpanded diameter which is smaller than the diameter of said blood vessel to allow said structural frame to be percutaneously placed into said blood vessel, said structural frame being expansible to form a generally cylindrical structural skeleton having a slightly larger diameter than said blood vessel to facilitate the securing of said structural skeleton in position in said blood vessel; and
an independently, percutaneously-insertable, expansible tubular member extending between first and second ends constructed to be percutaneously placed subsequent to the placement of said structural frame, said tubular member comprising a thin-walled flexible tubular membrane extending between said first and second ends, said membrane being essentially impermeable to blood and blood products, and means for expanding and holding said thin-walled flexible tubular membrane adjacent to the inside of said structural skeleton, in cooperative relationship therewith, in a manner that the outer surface of said thin-walled flexible tubular membrane is held in secure contact with the inside of said previously-placed structural skeleton.

2. A blood vessel wall-defining device for repairing an aneurysm in an aorta comprising in combination, a percutaneously-insertable structural frame extending between first and second ends having an unexpanded diameter sufficiently smaller than the diameter of said aorta to allow said structural frame to be percutaneously placed into said aorta, said structural frame being expansible to form a generally cylindrical structural skeleton having an expanded diameter of the order of 2 centimeters or more, said expanded diameter being slightly larger than the diameter of said aorta, to facilitate the securing of said structural skeleton in position in said aorta, said first and second ends of said structural skeleton being spaced about 10 centimeters or more apart; and an independently, percutaneously-insertable, expansible, tubular member extending between first and second ends, the distance between said first and second ends substantially corresponding to the distance between said first and second ends of said structural skeleton, and constructed to be percutaneously placed into said aorta subsequent to the placement of said structural frame, said tubular member comprising a thin-walled flexible tubular membrane extending between said first and second ends, said membrane being essentially impermeable to blood and blood products, and means for expanding and holding said thin-walled flexible tubular membrane adjacent to the inside of said structural skeleton, in cooperative relationship therewith, in a manner that the outer surface of said thin-walled flexible tubular membrane is held in secure contact with the inside of said previously-placed structural skeleton.

3. The device of claims 1 or 2 wherein said structural frame comprises first and second axially spaced end rings, said rings being each expansible to form a relatively stable retaining formation at each end of the device.

4. The device of claim 3 wherein said axially spaced end rings additionally comprise hooks constructed to engage the tissue of the vessel wall to aid in the securing of said rings to the inner wall of said blood vessel.

5. The device of claim 3 wherein said structural frame additionally comprises a plurality of strands arranged in a skeleton-defining pattern, said pattern extending between said first and second ends and being joined to said axially spaced end rings.

6. The device of claim 5 wherein said pattern of strands is of mesh form.

7. The device of claim 5 wherein said strands and rings of said structural frame are comprised of shape memory metal having a pliable low temperature state in which said structural frame is in unexpanded condition, and an expanded resiliently deformable relatively high temperature state, said high temperature corresponding to the body temperature of a mammal.

8. The device of claim 1 or 2 wherein said means for expanding and holding said thin-walled flexible tubular membrane of said tubular member comprises first and second axially spaced rings joined to said first and second ends of said thin-walled flexible tubular membrane, each of said rings being expansible to form a relatively stable retaining formation.

9. The device of claim 8 wherein said means for expanding and holding said thin-walled flexible tubular membrane of said tubular member further comprises,
struts axially disposed on the exterior of said thin-walled flexible tubular membrane, the ends of said struts being joined to said axially spaced first and second rings.

10. The device of claim 9 wherein said struts and said rings are comprised of shape memory metal having a pliable low temperature state in which said tubular member is in unexpanded condition, and an expanded resiliently deformable relatively high temperature state, said high temperature corresponding to the body temperature of a mammal.

11. The device of claim 8 wherein said means for expanding and holding said thin-walled flexible tubular membrane of said tubular member further comprises,
an expansible, open structural means disposed within the interior of said thin-walled flexible tubular membrane constructed to prevent the inward collapse of said thin-walled flexible tubular membrane from its expanded form.

12. The device of claim 11 wherein said open structural means is an outwardly expansible spring coil.

13. The device of claim 12 wherein said coil extends between said first and second axially spaced rings, respective ends of said coil being joined to said axially spaced rings.

14. The device of claim 13 wherein said coil and said rings of said tubular member are comprised of shape memory metal having a pliable low temperature state in which said tubular member is in unexpanded condition, and an expanded resiliently deformable relatively high temperature state, said high temperature corresponding to the body temperature of a mammal.

15. The device of claims 1 or 2 wherein said means for expanding and holding said thin-walled flexible tubular membrane of said tubular member further comprises,
first and second axially spaced rings joined to said first and second ends of said thin-walled flexible tubular membrane, each of said rings being expansible to form a relatively stable retaining formation;
struts axially disposed on the exterior of said thin-walled flexible tubular membrane, the ends of said struts being joined to said axially spaced first and second rings; and
an expansible, open structural means disposed within the interior of said thin-walled flexible tubular membrane constructed to prevent the inward collapse of said thin-walled flexible tubular membrane from its expanded form.

16. The device of claim 15 wherein said rings, said struts, and said open structural means of said tubular member are comprised of shape memory metal having a pliable low temperature state in which said thin-walled flexible tubular membrane is in unexpanded condition, and an expanded resiliently deformable and relatively high temperature state, said high temperature corresponding to the body temperature of a mammal.

17. The device of claims 1 or 2 wherein said thin-walled flexible tubular membrane comprises nylon mesh.

18. The device of claim 1 or 2 wherein said device includes insertion means for independently inserting said tubular member into said previously placed structural skeleton.

19. The device of claim 18 wherein said insertion means comprises an insertion catheter in which said tubular member is confined in reduced size for percutaneous insertion into the body.

20. A method for repairing an aneurysm in a blood vessel via interventional radiological techniques comprising the steps of:

determining the length of said aneurysm and the diameter of said blood vessel;

providing a structural frame extending between first and second ends having a diameter which is smaller than the diameter of said blood vessel, said structural frame being expansible to form a generally cylindrical structural skeleton having a slightly larger diameter than said blood vessel;

inserting said structural frame percutaneously in unexpanded form into said blood vessel at a site proximal or distal to said aneurysm and moving said structural frame to the site of said aneurysm;

causing the expansion of said frame to form said structural skeleton, and anchoring at least said first and second ends to the walls of said blood vessel above and below said aneurysm;

providing an expansible tubular member extending between first and second ends, said tubular member comprising a thin-walled flexible tubular membrane extending between said first and second ends, said thin-walled flexible tubular membrane being essentially impermeable to blood and blood products, and means for expanding and holding said thin-walled flexible tubular membrane adjacent to the inside of said structural skeleton;

independently inserting said tubular member percutaneously in unexpanded form into said blood vessel at a site distal to said aneurysm and moving said tubular member into said structural skeleton previously disposed within said blood vessel; and causing the expansion and anchoring of said tubular member adjacent the inside of said structural skeleton, the outer surface of said tubular member engaging said structural skeleton, whereby the combination of said structural skeleton and said tubular member cooperate to define a graft-form section of said blood vessel that isolates said aneurysm from hemodynamic pressure.

21. The method of claim 20 wherein said blood vessel is the abdominal aorta.

22. A method for repairing an aneurysm in an aorta via interventional radiological techniques comprising the steps of:

determining the length of said aneurysm and the diameter of said aorta;

providing a structural frame extending between first and second ends having a diameter sufficiently smaller than the diameter of said aorta to allow said structural frame to be percutaneously introduced into said aorta, said structural frame being expansible to form a generally cylindrical structural skeleton having an expanded diameter of the order of 2 centimeters or more, said expanded diameter being slightly larger than the diameter of said aorta, and there being a distance between said first and second ends of said structural skeleton of about 10 centimeters or more;

inserting said structural frame percutaneously in unexpanded form into said aorta at a site proximal or distal to said aneurysm and moving said structural frame to the site of said aneurysm;

causing the expansion of said frame to form said structural skeleton, and anchoring at least said first and second ends to the walls of said blood vessel above and below said aneurysm;

providing an expansible, tubular member extending between first and second ends, the distance between said first and second ends being substantially the same as the distance between said first and second ends of said structural skeleton, said tubular member comprising a thin-walled flexible tubular membrane extending between said first and second ends, said thin-walled flexible tubular membrane being essentially impermeable to blood and blood products, and means for expanding and holding said thin-walled flexible tubular membrane adjacent to the inside of said structural skeleton;

independently inserting said tubular member percutaneously in unexpanded form into said blood vessel at a site distal to said aneurysm and moving said tubular member into said structural skeleton previously disposed within said blood vessel; and causing the expansion and anchoring of said tubular member adjacent the inside of said structural skeleton, the outer surface of said tubular member engaging said structural skeleton, whereby the combination of said structural skeleton and said tubular member cooperate to define a graft-form section of said aorta that isolates said aneurysm from hemodynamic pressure.

* * * * *